United States Patent
Tamura et al.

(10) Patent No.: US 8,095,211 B2
(45) Date of Patent: Jan. 10, 2012

(54) BODY FAT MEASURING DEVICE

(75) Inventors: Hideki Tamura, Moriyama (JP); Satoru Inakagata, Nara (JP); Shuji Murakami, Takaishi (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 904 days.

(21) Appl. No.: 11/814,321

(22) PCT Filed: Jan. 25, 2006

(86) PCT No.: PCT/JP2006/301136
§ 371 (c)(1),
(2), (4) Date: Jul. 19, 2007

(87) PCT Pub. No.: WO2006/080345
PCT Pub. Date: Aug. 3, 2006

(65) Prior Publication Data
US 2009/0018463 A1    Jan. 15, 2009

(30) Foreign Application Priority Data
Jan. 26, 2005   (JP) ................................ 2005-018721

(51) Int. Cl.
*A61B 5/05* (2006.01)
(52) U.S. Cl. ..................................................... 600/547
(58) Field of Classification Search ............. 600/547, 600/587, 595
See application file for complete search history.

(56) References Cited

U.S. PATENT DOCUMENTS

| | | | |
|---|---|---|---|
| 6,487,445 B1 * | 11/2002 | Serita et al. ................... | 600/547 |
| 6,526,315 B1 | 2/2003 | Inagawa et al. | |
| 7,283,869 B2 | 10/2007 | Onda et al. | |
| 2003/0158501 A1 | 8/2003 | Uchida et al. | |
| 2004/0077969 A1 * | 4/2004 | Onda et al. ................... | 600/547 |
| 2004/0152962 A1 | 8/2004 | Kondoh et al. | |
| 2005/0197575 A1 * | 9/2005 | Kondoh et al. ............... | 600/438 |
| 2005/0281441 A1 * | 12/2005 | Martinsen et al. ............ | 382/124 |

FOREIGN PATENT DOCUMENTS

CN    1492744    4/2004

(Continued)

OTHER PUBLICATIONS

English language Abstract of JP 200014655, Jan. 18, 2000.

(Continued)

*Primary Examiner* — Max HIndenburg
*Assistant Examiner* — Jonathan M Foreman
(74) *Attorney, Agent, or Firm* — Greenblum & Bernstein, P.L.C.

(57) ABSTRACT

A body fat measuring device comprises electrodes brought into contact with the waist portion of a subject, an optical sensor composed of a light applying section and a light receiving section, an impedance computing section for computing the impedance between the electrodes, a subcutaneous fat thickness computing section for computing the thickness of the subcutaneous fat of the subject from the value detected by the optical sensor, and a body fat computing section which subtracts the amount of subcutaneous fat determined using the thickness of the subcutaneous fat computed by the subcutaneous thickness computing section from the total fat amount of the subject determined using the impedance computed by the impedance computing section so as to determine the visceral fat amount of the subject. With this, not only the accuracy of measurement of the visceral fat amount is improved but also the visceral fat amount of the subject can be easily computed even without a database.

11 Claims, 4 Drawing Sheets

FOREIGN PATENT DOCUMENTS

| | | |
|---|---|---|
| EP | 1136037 | 9/2001 |
| EP | 1269917 | 1/2003 |
| EP | 1396227 | 3/2004 |
| JP | 3035791 | 6/1998 |
| JP | 11-123182 | 5/1999 |
| JP | 200014655 | 1/2000 |
| JP | 2000-175875 | 6/2000 |
| JP | 2000350710 | 12/2000 |
| JP | 3396663 | 7/2001 |
| JP | 2001-212111 | 8/2001 |
| JP | 2001-252257 | 9/2001 |
| JP | 2002-369806 | 12/2002 |
| JP | 2002369806 | 12/2002 |
| JP | 2003-159227 | 6/2003 |
| JP | 2003-169783 | 6/2003 |
| JP | 2003169783 | 6/2003 |
| WO | 01/76485 | 10/2001 |
| WO | 0176485 | 10/2001 |

OTHER PUBLICATIONS

English language Abstract of WO 02065900, Aug. 29, 2002.
Japanese Office Action, dated Sep. 7, 2010 along with an English translation thereof.
English language Abstract of JP 2002-369806, Dec. 24, 2002.
English language Abstract of JP 2001-178697, Mar. 7, 2001.
English language Abstract of WO 9823916, Apr. 6, 1998.
English language Abstract of JP 2000-350710, Dec. 19, 2000.
English language Abstract of JP 2003-169783, Jun. 17, 2003.
English language Abstract of JP 11-123182, May 11, 1999.

* cited by examiner

BODY FAT MEASURING DEVICE

TECHNICAL FIELD

The present invention relates to a body fat measuring device for measuring body fat of a human body.

BACKGROUND ART

As a method for measuring body fat (subcutaneous fat, visceral fat) safely and easily, a technique utilizing measurement of biological impedance (BI) and a technique utilizing a difference between muscle and fat in light absorption rate by applying light to the human body and measuring subcutaneous fat based on the amount of reflected light are known.

For example, Patent Publication No. 3396663 (Patent document 1) discloses a body fat measuring device in which a plurality of electrodes are disposed around a waist portion of the subject and voltage generated by passing an current between specific electrodes is measured, thereby computing impedance, in turn, fat amount.

Patent Publication No. 3035791 (Patent document 2) discloses a method and a device for measuring subcutaneous fat thickness of the human body by means of light.

Unexamined Patent Publication No. 2000-350710 (Patent document 3) discloses a method and a device for computing the visceral fat by measuring the subcutaneous fat thickness using an impedance method and an ultrasonic means.

Unexamined Patent Publication No. 2003-169783 (Patent document 4) discloses a device for measuring the subcutaneous fat thickness according to an optical method.

However, in the device disclosed in Patent document 1, a total fat amount of the waist portion of the subject is measured and a visceral fat amount is estimated from a measured value on the basis of correlation between the total fat amount and the visceral fat amount. In this case, the visceral fat cannot be separated from the subcutaneous fat in the impedance measurement, and they are separated from each other according to estimation based on personal physical information (height, waist circumference, etc.). Patent document 1 also discloses another device in which electrodes for current application are disposed on front and back surfaces of the waist portion, electrodes for voltage detection are disposed on side surfaces and voltage between the electrodes is measured to compute the visceral fat amount. In this case, since the measured value greatly varies depending on the position of the electrodes for voltage detection, an error caused by variation due to individual difference among the subjects having different waist portion shapes and waist circumferences becomes larger.

The device disclosed in Patent document 2 can measure only the subcutaneous fat thickness and basically cannot measure the visceral fat amount.

In the devices disclosed in Patent documents 3, 4, the total fat amount is measured by attaching electrodes to hands and feet according to the impedance method. Thus, in both the Patent documents 3, 4, a site to be measured is not directly measured and the total fat amount is computed based on correlation. As a result, the measurement accuracy is not so satisfactory.

Moreover, in the devices for computing the total fat amount according to the impedance method, it is necessary to provide a database on the relation between the impedance measured in the state where the electrodes are attached to hands and feet and the body fat amount and the total fat amount is computed from the impedance measured at hands and feet on the basis of the database. For this reason, a complicated operation of preparing the database is required.

DISCLOSURE OF INVENTION

To solve the above-mentioned conventional problems, an object of the present invention is to provide a body fat measuring device which can improve the measurement accuracy of the visceral fat amount and easily obtain the visceral fat amount of the subject without the necessity for preparing a database.

To achieve the above-mentioned object, a body fat measuring device for measuring visceral fat amount of a subject according to the present invention has a plurality of electrodes brought into contact with a waist portion of the subject, an impedance measuring means for measuring an impedance between the electrodes, an optical sensor formed of a light applying section for applying light to the waist portion of the subject and a light receiving section for receiving reflected light, a subcutaneous fat thickness measurement means for measuring a subcutaneous fat thickness of the subject on the basis of a value detected by the optical sensor, and a body fat computing means for computing the visceral fat amount by subtracting the subcutaneous fat amount based on the subcutaneous fat thickness measured by the subcutaneous fat thickness measurement means from a total fat amount of the subject which is obtained from the impedance measured by the impedance measuring means.

According to the present invention, the waist portion total fat amount of a site to be measured in the waist portion of the subject is directly measured by using the impendence method, and the subcutaneous fat thickness of the site to be measured in the waist portion is also directly measured by the optical sensor and the subcutaneous fat amount is computed from the detected value. Then, by subtracting the computed subcutaneous fat amount from the waist portion total fat amount thus obtained, the visceral fat amount can be computed. In this manner, since the subcutaneous fat thickness (or the subcutaneous fat amount) measured by the optical sensor can be adopted as one of parameters for correction based on physical characteristics, the visceral fat amount can be measured with higher accuracy. By merely subtracting the subcutaneous fat amount from the total fat amount obtained by directly measuring the waist portion as the site to be measured, the visceral fat amount can be easily measured without a database.

It is preferred to provide plural sets of electrodes brought into contact with different opposed positions on the waist portion of the subject. Thus, it becomes possible to take account of the shape of the body fat, improving the measurement accuracy.

It is preferred to provide plural sets of optical sensors for measuring the subcutaneous fat thickness of the subject at different positions of the waist portion of the subject. Thus, since the distribution of the subcutaneous fat thickness in the site to be measured is found, it becomes possible to take account of the distribution of the subcutaneous fat thickness, improving the measurement accuracy of the body fat.

It is preferred that a support member attached along the circumference of the waist portion of the subject is provided and the optical sensor can move relative to the support member. Thus, by moving the optical sensor relative to the support member attached along the waist portion of the subject, the subcutaneous fat thickness can be measured at each moved position. For this reason, it becomes possible to take account of the distribution of the subcutaneous fat thickness on the whole waist portion, improving the measurement accuracy of the body fat.

It is preferred that the electrodes and the optical sensor are gathered on one place. Since the subcutaneous fat thickness can be measured at the site where impedance is measured, the body fat amount can be measured with higher accuracy. Furthermore, since measurement of impedance and measurement according to an optic method can be performed substantially simultaneously, the subject is in the same position at the time of measurement. Thus, impedance and the subcutaneous fat thickness can be measured stably and the total fat amount, the subcutaneous fat amount and the visceral fat amount can be measured with higher accuracy. Moreover, the electrodes and the optical sensor can be disposed on the same place of the same member, the number of parts in the body fat measuring device can be reduced and handling is simplified.

It is preferred that the electrodes and the optical sensor are disposed, a band-like support member attached to the waist portion of the subject is provided and the support member has a pressure adjustment means for adjusting pressure when being attached to the waist portion of the subject. Thus, since measurement of impedance and measurement of the subcutaneous fat thickness by means of light irradiation can be performed in the optimum pressure state with respect to the waist portion of the subject, the measurement accuracy can be improved.

It is preferred that the plurality of electrodes are a pair of current-conducting electrodes and a pair of electrodes for voltage detection and the impedance measuring means measures the impedance of the waist portion on the basis of a current flowing between the current-conducting electrodes and voltage between the electrodes for voltage detection.

BEST MODE FOR CARRYING OUT THE INVENTION

Figure 1:
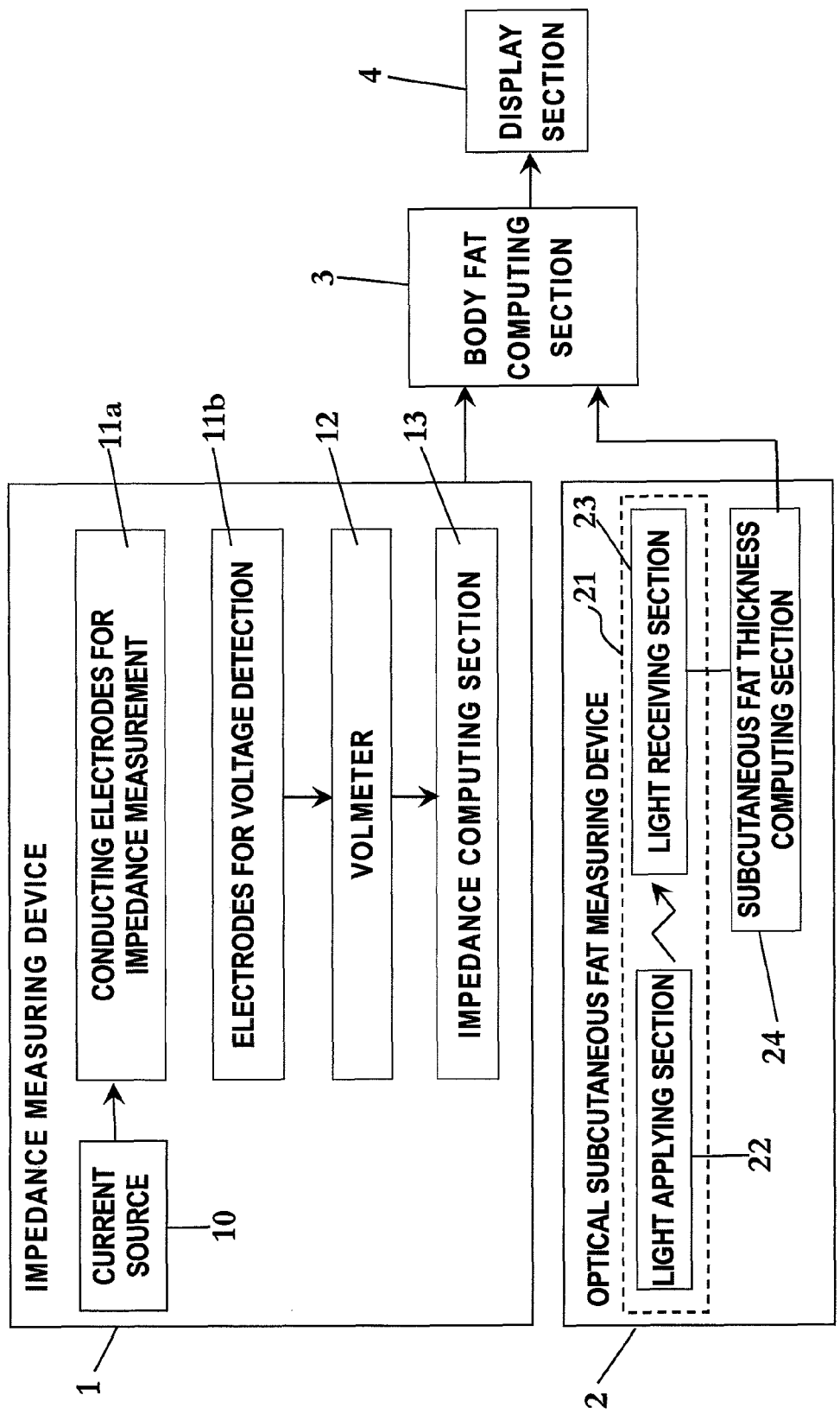
FIG. 1 is a control block diagram of body fat measurement in accordance with an embodiment of the present invention.
Figure 2:
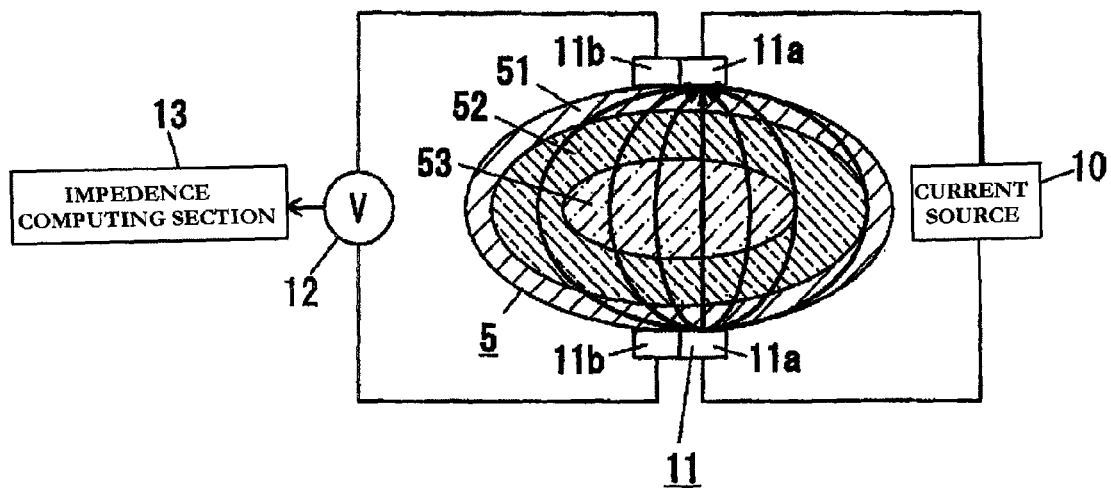
FIG. 2 is a configuration view of measurement of impedance by an impedance measuring device in this device.
Figure 3:
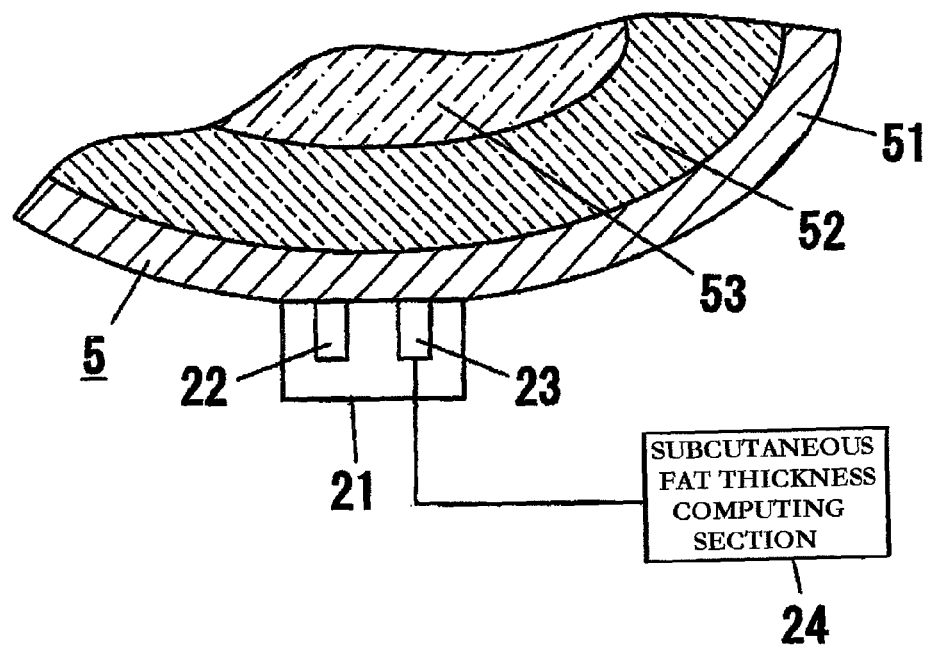
FIG. 3 is a configuration view of measurement of a subcutaneous fat thickness by an optical subcutaneous fat measuring device in this device.

A body fat measuring device (hereinafter, referred to as this device) in accordance with an embodiment of the present invention will be described below with reference to figures. FIG. 1 shows control block configuration of the device, FIG. 2 shows configuration of an impedance measuring device in this device and FIG. 3 shows configuration of an optical subcutaneous fat measuring device in this device.

The body fat measuring device, as shown in FIG. 1, serves to measure the visceral fat amount of the subject has an impedance measuring device (impedance measuring means) for measuring the impedance between electrodes, an optical subcutaneous fat measuring device 2 (subcutaneous fat measuring means), a body fat computing section 3 (body fat computing means) for computing body fat on the basis of values measured by these measuring devices and a display section 4 for displaying the computed body fat.

The impedance measuring device has a current source 10, a plurality of electrodes 11 brought into contact with the waist portion of the subject, a voltmeter 12 and an impedance computing section 13 for computing the impedance between the electrodes. The plurality of electrodes 11 has a pair of conducting electrodes for impedance measurement 11a and a pair of electrodes for voltage detection 11b for the waist portion while being conducted. The current source 10 flows a current from the pair of conducting electrodes 11a to the waist portion. The voltmeter 12 detects voltage between the pair of electrodes for voltage detection 11b.

The optical subcutaneous fat measuring device 2 has an optical sensor 21 composed of a light applying section 22 for applying light into tissues of the waist portion from the surface of the waist portion of the subject and a light receiving section 23 for receiving light reflected from the waist portion tissues, and a subcutaneous fat thickness computing section 24 for measuring a subcutaneous fat thickness of the waist portion of the subject on the basis of a detected value by the optical sensor 21, that is, light-receiving information. The body fat computing section 3 computes the visceral fat amount of the subject by subtracting a subcutaneous fat amount based on the subcutaneous fat thickness computed by the subcutaneous fat thickness computing section 24 from a total fat amount of the subject determined using the impedance computed by the impedance computing section 13. For example, an infrared emitting element for applying an infrared ray is used as the light applying section 22.

FIG. 2 and FIG. 3 each show a mode in which the impedance measuring device 1 and the optical subcutaneous fat measuring device 2 are attached to the waist portion of the subject to measure the body fat. The figures schematically show the cross section of the waist portion 5 of the subject as a site to be measured. The waist portion 5 of the subject has a subcutaneous fat 51 on the outer periphery thereof, a muscle 52 inner of the subcutaneous fat 51 and a visceral fat 53 inner of the muscle 52.

The pair of conducting electrodes 11a of the impedance measuring device 1 are brought into contact with the waist portion 5 as the site to be measured of the subject and the pair of for voltage detection electrodes 11b are brought into contact with the waist portion 5. In this case, the pair of conducting electrodes 11a each are brought into contact with the waist portion 5 as opposed to each other across the waist portion 5 so that a current may flow through the visceral fat 53 when the current is passed to the waist portion 5 through the electrodes 11a. In the mode shown in FIG. 2, the pair of electrodes for voltage detection 11b are disposed next to the pair of conducting electrodes 11a so as to be opposed to each other across the waist portion 5.

The current source 10 passes a current to the waist portion 5 of the subject through the conducting electrodes 11a, thereby generating voltage. The voltmeter 12 measures the voltage. The impedance computing section 13 computes an impedance value between the pair of electrodes 11 on the basis of the current flowing between the electrodes 11a and the voltage measured by the voltmeter 12.

In this case, the current flowing through the waist portion 5 between the pair of conducting electrode 11a disposed as opposed to each other across the waist portion 5 is passed so as to spread as represented by arrows in FIG. 2. For this reason, the computed impedance is a joint impedance between the portions opposed to each other across the waist portion 5, which is based on the total fat amount of the cross section of the waist portion 5. Thus, as the total fat amount (subcutaneous fat+visceral fat) is increased, the joint impedance becomes larger and as the total fat amount is decreased, the joint impedance becomes smaller.

In this embodiment, the light receiving section 23 in the optical sensor 21 of the optical subcutaneous fat measuring device 2 is located in the vicinity of the light applying section 22. The light applying section 22 and the light receiving section 23 are brought into contact with the waist portion 5 as the site to be measured of the subject, and light applied by the light applying section 22 disperses on the subcutaneous fat 51 and is absorbed into the muscle 52 inner of the subcutaneous fat 51. Thus, when the subcutaneous fat 51 is thin, less light applied by the light applying section 22 disperses toward the surface of the skin, and less light returns toward the surface of the skin and spreads less widely. As a result, the light amount reaching the light receiving section 23 becomes smaller. On the contrary, when the subcutaneous fat 51 is thick, more light applied by the light applying section 22 disperses, and more light returns toward the surface of the skin and spreads more widely. As a result, the light amount reaching the light receiving section 23 becomes larger.

Based on the light-receiving information in the light receiving section 23, the subcutaneous fat thickness computing section 24 computes the thickness of the subcutaneous fat 51. In this manner, the subcutaneous fat thickness of the waist portion 5 of the subject as the site to be measured can be measured directly.

As described above, the total fat amount of the subject is obtained on the basis of the impedance determined by directly measuring the waist portion 5 as the site to be measured of the subject using the impedance measuring device 1. Furthermore, the subcutaneous fat amount is obtained on the basis of data on the subcutaneous fat thickness of the waist portion 5 determined by directly measuring the waist portion 5 as the site to be measured using the optical subcutaneous fat measuring device 2. The body fat computing section 3 computes the visceral fat amount of the subject by subtracting the subcutaneous fat amount from the total fat amount thus obtained. The visceral fat amount thus obtained of the subject is displayed on the display section 4.

Here, by performing corrections according to physical characteristics such as height and waist circumference of the subject in addition to subtracting the subcutaneous fat thickness (subcutaneous fat amount) of the subject directly measured by the optical subcutaneous fat measuring device 2 from the total fat amount, the visceral fat amount can be measured with higher accuracy. In this case, data on relation between the physical characteristics such as height and waist circumference and the body fat amount may be stored in a database and based on the data, corrections may be made according to the physical characteristics such as height and waist circumference of the subject. Moreover, data on the subcutaneous fat thickness (subcutaneous fat amount) may be also stored in the database.

According to the present invention, even when the database is provided, by adopting the waist portion 5 of the human body as the model as shown in FIG. 2, the total fat amount of the subject is obtained based on the impedance and the subcutaneous fat amount of the subject is obtained based on the subcutaneous fat thickness. Thus, unless the database is provided, the body fat computing section 3 can easily measure the visceral fat amount merely by subtracting the subcutaneous fat amount from the total fat amount.

In the above-mentioned embodiment, the site to be measured with respect to the subcutaneous fat thickness is a single site on the waist portion 5. However, by measuring subcutaneous fat at a plurality of sites (umbilicus, back, side and other areas), the distribution of the subcutaneous fat on the circumference of the waist portion 5 is found. Thus, the measurement accuracy of the subcutaneous fat amount is improved. As a result, the computation accuracy of the visceral fat amount is also improved.

Figure 4:
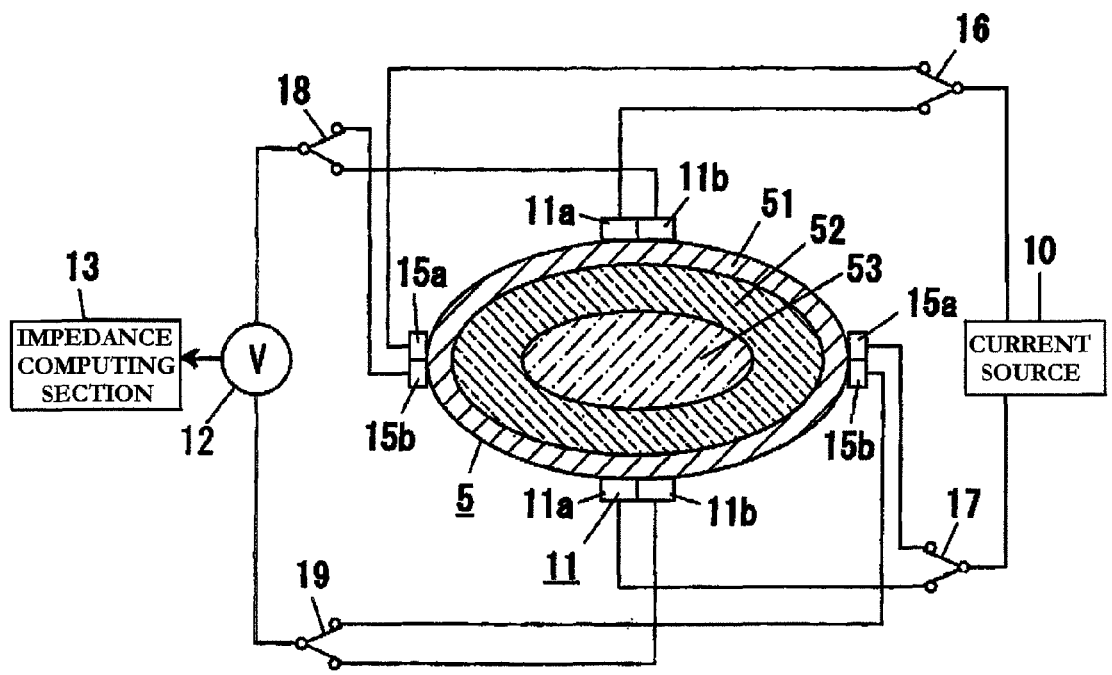
FIG. 4 is a configuration view of an impedance measuring device in a body fat measuring device in accordance with another embodiment of the present invention.

FIG. 4 shows another embodiment in which the impedance measuring device 1 is attached to the waist portion of the subject to measure body fat. In this embodiment, an impedance are measured at a plurality of sites. That is, plural sets (two sets in this embodiment) of the pair of conducting electrodes 11a are provided and the plural sets of the electrodes 11a are brought into contact with different positions on the waist portion 5 as the site to be measured. For example, one set of the pair of electrodes 11a are brought into contact with front and back surfaces of the waist portion 5 so as to place the waist portion 5 therebetween and the other set of the pair of electrodes 11a are brought into contact with right and left side surfaces of the waist portion 5 so as to place the waist portion 5 therebetween. In this embodiment, plural sets (two sets in this embodiment) of the pair of electrodes for voltage detection 11b are located in the vicinity of the corresponding sets of the conducting electrodes 11a.

In this embodiment, the plural sets of electrodes are switched in time series by using switches so as to measure the impedance between the electrodes in two dimensions. In addition to the components shown in FIG. 2, the impedance measuring device 1 has a pair of conducting electrodes 15a, a pair of electrodes for voltage detection 15b, switches for switching conduction 16, 17 and switches for switching voltage detection 18, 19. A current is passed between one pair of conducting electrodes 11a and voltage between one pair of electrodes for voltage detection 11b is measured by the voltmeter 12 to obtain the impedance. By switching the switches 16, 17, 18, 19, a current is passed between the other pair of conducting electrodes 11a and a voltage between the other pair of electrodes for voltage detection 11b is measured by the voltmeter 12 to obtain the impedance. In this manner, the body fat amount is found in two dimensions. Thus, subcutaneous fat distribution and visceral fat distribution can be easily imaged and the images can be displayed on the display section 4. As a result, since it is possible to offer visual presentation of the subcutaneous fat amount and the visceral fat amount to the subject, the subject is easy to recognize that.

Figure 5:
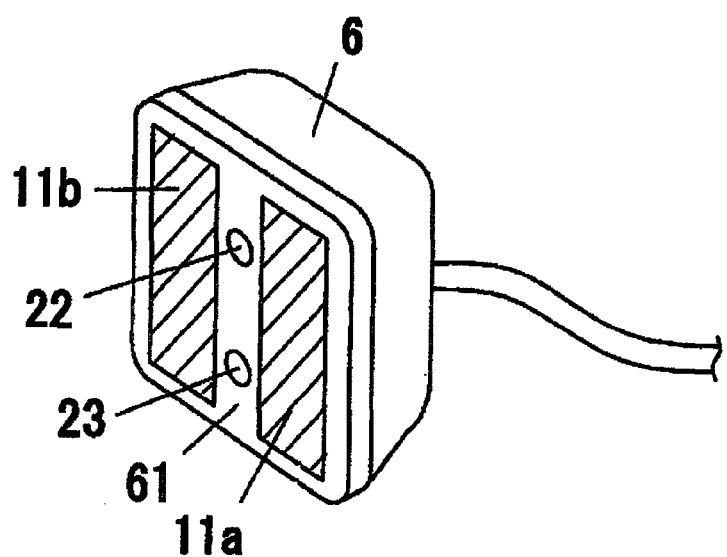
FIG. 5 is a perspective view of a body fat measuring device in accordance with still another embodiment of the present invention.

FIG. 5 shows a body fat measuring device in accordance with still another embodiment of the present invention. In this embodiment, the electrodes for impedance measurement 11a, 11b brought into contact with the waist portion 5 in the impedance measuring device 1, and the light applying section 22 and the light receiving section 23 in the optical subcutaneous fat measuring device 2 are gathered in one place as a probe 6. Two probes 6 having the same configuration are attached to the waist portion so as to hold the waist portion therebetween. In each of the probes 6, the electrodes 11a, 11b, the light applying section 22 and the light receiving section 23 are gathered on a contact surface 61 which contacts with the waist portion 5.

In this embodiment, since an impedance measurement site is the same as a subcutaneous fat measurement site, the subcutaneous fat thickness can be measured at the site where impedance is measured and thus, the body fat amount can be measured with higher accuracy. Furthermore, measurement of impedance and measurement according to an optic method can be performed substantially simultaneously, the subject is in the same position at the time of measurement. Thus, since impedance and the subcutaneous fat thickness can be measured stably and the total fat amount, the subcutaneous fat amount and the visceral fat amount can be measured with higher accuracy. Moreover, the electrodes 11a, 11b and other elements are gathered on the contact surface 61 of the probe 6 which contacts with the waist portion 5, the number of parts in the body fat measuring device can be reduced, handling is simplified and measurement time can be shortened, reducing loads to the subject.

Figure 6:
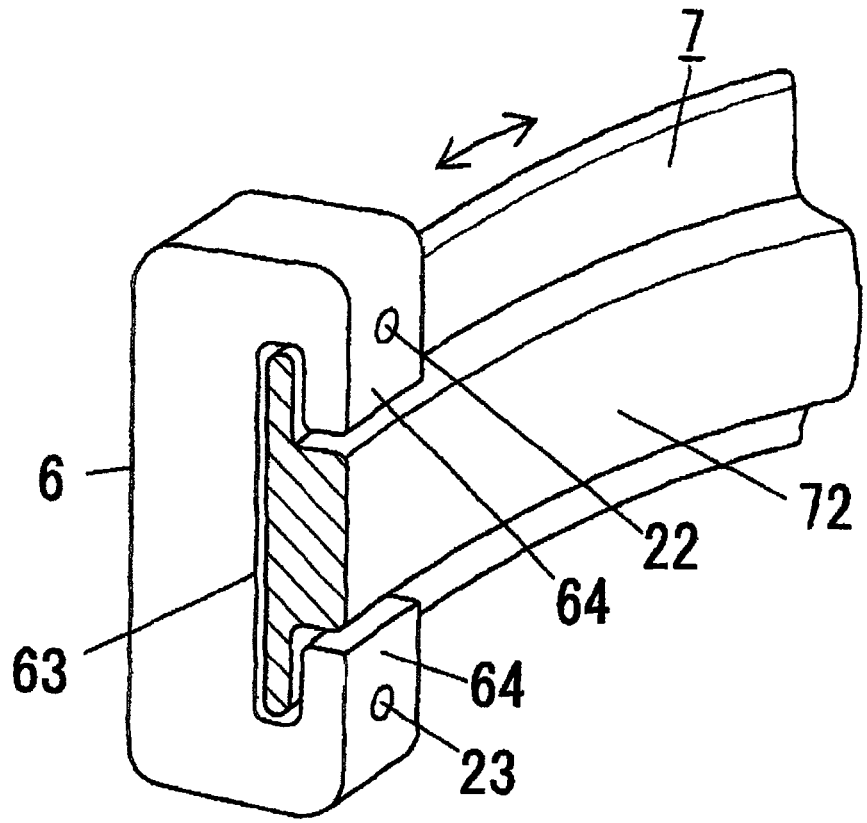
FIG. 6 is a perspective view of a main part of a body fat measuring device in accordance with still another embodiment of the present invention.

FIG. 6 shows an optical subcutaneous fat measuring device in accordance with still another embodiment of the present invention. This device has the probe 6 including the light applying section 22 and the light receiving section 23 and a band-like long support member 7 movably supporting the probe 6. The deformable support member 7 can be disposed along the circumference of the waist portion 5 of the subject and has a means for being detachably attached to the waist portion 5 (not shown). An inner projection rail 72 is formed on the center of the inner surface of the support member 7 so as to protrude inwards and a C-like groove 63 is formed on the probe 6. The probe 6 can freely move in the longitudinal direction by engaging the C-like groove 63 with the band-like support member 7. A protrusion 64 is formed at each of upper and lower ends of an inner opening of the probe 6. These protrusions 64 each are provided with the light applying section 22 and the light receiving section 23. The inner projection rail 72 is located between the protrusions 64 and is substantially flush with the protrusions 64. Thus, when the support member 7 is brought into contact with the waist portion 5, the light applying section 22 and the light receiving section 23 contact with the waist portion 5.

In this embodiment, by moving the probe 6 along the support member 7 in the state where the band-like support member 7 is disposed and attached along the circumference of the waist portion 5 of the subject, the probe 6 can be moved along the circumference of the waist portion 5 to sequentially measure the amount of received light. Thus, the subcutaneous fat thickness in the cross section of the waist portion 5 can be accurately measured at each site on the circumference of the waist portion 5, thereby obtaining the accurate subcutaneous fat amount. When a means for measuring movement of the probe 6 is provided and the movement of the probe 6 is measured, peripheral length of the waist portion 5 can be automatically measured and the subcutaneous fat amount can be computed based on subcutaneous fat thickness information and peripheral length information of the waist portion 5. Alternatively, when movement and movement direction of the probe 6 is measured by using an acceleration sensor or the like, contour shape information of the waist portion 5 can be obtained and a detailed image can be drawn at imaging.

Figure 7:
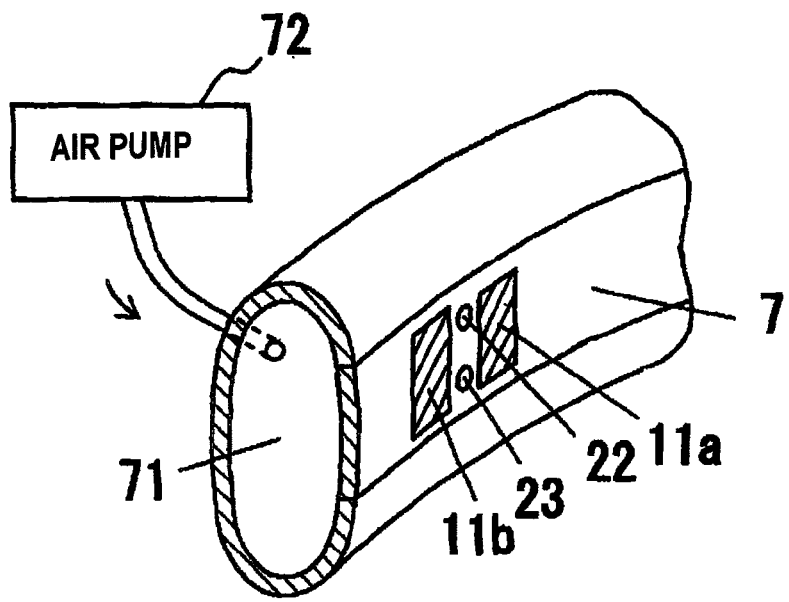
FIG. 7 is a perspective view of a main part of a body fat measuring device in accordance with still another embodiment of the present invention.

FIG. 7 shows a body fat measuring device in accordance with still another embodiment of the present invention. The device in this embodiment has the band-like support member 7 having deformability so as to be attached to the waist portion 5 of the subject, and the electrodes for impedance measurement 11a, 11b, the light applying section 22 and the light receiving section 23 for measurement according to the optical method are provided on the inner surface of the support member 7. The support member 7 has a pressure adjustment means for adjusting pressure when being disposed and attached along the waist portion 5 of the subject. The pressure adjustment means can be comprised of the support member 7 formed of a tube as a hollow part 71, an air feed means formed of an air pump 72 for feeding air into the hollow part 71 and a pressure sensor (not shown) provided at the support member 7.

In this embodiment, the band-like support member 7 formed of a tube is disposed and attached along the circumference of the waist portion 5 of the subject, and then, the air pump 72 forming the pressure adjustment means feeds air into the hollow part 71 of the support member 7 and the pressure sensor measures contact pressure of the support member 7 against the waist portion 5 to adjust the air feed amount of. Thereby, the contact pressure of the electrodes 11a, 11b, the light applying section 22 and the light receiving section 23 against the waist portion 5 can be adjusted to be the contact pressure suitable to each of the impedance method and the optical method. Since measurement of impedance and measurement of the subcutaneous fat thickness by means of light irradiation can be performed in the optimum pressure state with respect to the waist portion 5 of the subject, the measurement accuracy can be improved.

The present invention is not limited to the configuration of the above-mentioned embodiments and can be modified so as not to change the subject matter of the invention. This application is based on Japanese Patent Application No. 2005-018721 and the whole contents of the application are incorporated into this application by reference.

The invention claimed is:

1. A body fat measuring device that measures a visceral fat amount of a subject, comprising:
   a plurality of electrodes that are contactable with a waist portion of the subject;
   an impedance measurer that measures an impedance between a subset of the plurality of electrodes;
   at least one optical sensor that includes a light source that is configured to apply light to the waist portion of the subject and a light receiver that receives reflected light, the plurality of electrodes and the at least one optical sensor being configured to be provided at a single location;
   a subcutaneous fat thickness measurer that measures a subcutaneous fat thickness of the subject based on a value detected by the at least one optical sensor; and
   a body fat determiner that computes the visceral fat amount by subtracting a subcutaneous fat amount that is determined based on the subcutaneous fat thickness measured by the subcutaneous fat thickness measurer from a total fat amount of the subject which is obtained from the impedance measured by the impedance measurer,
   wherein the plurality of electrodes include plural sets of electrodes that are configured to be contactable with different directly opposing positions on the waist portion of the subject;
   wherein the plurality of electrodes includes a first pair of conductive electrodes that are configured to be directly opposed to each other across the waist portion of the subject for measuring the impedance,
   wherein the plurality of electrodes includes a second pair of conductive electrodes that are configured to be directly opposed to each other across the waist portion of the subject and between which voltage is detected, and
   wherein each of the second pair of conductive electrodes adjoin corresponding electrodes from the first pair of conductive electrodes.

2. The body fat measuring device according to claim 1, wherein the impedance measurer measures the impedance in two dimensions by switching the first pair of conductive electrodes in accordance with a time series.

3. The body fat measuring device according to claim 1,
wherein the light source included in the at least one optical sensor is configured to apply light to different positions on the waist portion of the subject to measure the subcutaneous fat thickness at the different positions based on the reflected light received.

4. The body fat measuring device according to claim 1,
wherein a support member is attachable along a circumference of the waist portion of the subject, and
wherein the at least one optical sensor is movable relative to the support member.

5. The body fat measuring device according to claim 1,
wherein the plurality of electrodes and the at least one optical sensor are attachable to a band-like support member that is attachable to the waist portion of the subject, and
wherein the support member has a pressure adjuster that adjusts a pressure of the band-like support member.

6. The body fat measuring device according to claim 1,
wherein the impedance measurer measures the impedance based on a current flowing between the first pair of conductive electrodes and a voltage detected between the second pair of conductive electrodes, and
wherein the impedance is measured based on the waist portion of the subject.

7. The body fat measuring device according to claim 6,
wherein the impedance measurer measures the impedance in two dimensions by switching the first pair of conductive electrodes in accordance with a time series.

8. The body fat measuring device according to claim 6,
wherein the light source included in the at least one optical sensor is configured to apply light to different positions on the waist portion of the subject and to measure the subcutaneous fat thickness at the different positions based on the reflected light received.

9. The body fat measuring device according to claim 6,
wherein a support member is attachable along a circumference of the waist portion of the subject, and
wherein the at least one optical sensor is movable relative to the support member.

10. The body fat measuring device according to claim 6,
wherein the at least one optical sensor is disposed between one of the first pair of conductive electrodes and one of the second pair of conductive electrodes.

11. The body fat measuring device according to claim 6,
wherein the plurality of electrodes and the at least one optical sensor are attachable to a band-like support member that is attachable to the waist portion of the subject, and
wherein the support member has a pressure adjuster that adjusts a pressure of the band-like support member.

* * * * *